United States Patent
Nam

(10) Patent No.: US 6,896,912 B2
(45) Date of Patent: May 24, 2005

(54) NATURAL TEA FOR CURING MEN'S IMPOTENCE AND A METHOD FOR MANUFACTURING THE SAME

(76) Inventor: Jong-Hyun Nam, 26-5, Koyo-dong, Songpa-ku, Seoul 138-110 (KR)

( * ) Notice: Subject to any disclaimer, the term of this patent is extended or adjusted under 35 U.S.C. 154(b) by 0 days.

(21) Appl. No.: 10/441,797

(22) Filed: May 20, 2003

(65) Prior Publication Data

US 2003/0206977 A1 Nov. 6, 2003

Related U.S. Application Data

(62) Division of application No. 09/830,010, filed on Apr. 19, 2001, now Pat. No. 6,680,075.

(30) Foreign Application Priority Data

Aug. 20, 1999 (KR) ........................................ 1999-34615

(51) Int. Cl.$^7$ ............................................. A61K 35/78
(52) U.S. Cl. ....................................................... 424/725
(58) Field of Search ............................. 424/195.1, 725

(56) References Cited

FOREIGN PATENT DOCUMENTS

| CN | 1107715 | 9/1995 |
|---|---|---|
| JP | 58-83689 | 5/1983 |
| JP | 02170057 | 2/1992 |
| KR | 1990-8983 | 7/1990 |
| KR | 1994-6487 | 4/1994 |
| KR | 1998-61413 | 10/1998 |
| KR | 1998-66401 | 10/1998 |

OTHER PUBLICATIONS

Malini et al. "Antifertility Effects of Beta–Sitosterol in Male Albino Rats." *Journal of Ethnopharmacology.* 35(1991): 149–153.

Sanada et al. "Comparative Studies on the Constituents of the Parasitic Plant and its Host (II) in the Constituents of the Root of Alnus Maximowiczii Callier (I)" *Shoyakugaku Zasshi.* 41.1 (1987): 80–83.

Talapatra et al. "Triterpenoid and Related Compounds, Part XXIII: Triterpenoid Constituents of Alnus Nepalenis D.don" *Indian Chem Soc.* 60.2(1983):203.

*Primary Examiner*—Patricia Leith
(74) *Attorney, Agent, or Firm*—Renner, Otto, Boisselle & Sklar, LLP

(57) ABSTRACT

Disclosed are a natural invigorating tea and a method for preparing the same. The natural invigorating tea may be in the form of powder, liquid, or granules and is made of parasitic herb, and alder and/or *schizandrae fructus*, optionally supplemented with *torilis fructus* and/or *polygalae japonica herba*. Taking of the tea at least twice a day, morning and evening, invigorates human body.

5 Claims, No Drawings

NATURAL TEA FOR CURING MEN'S IMPOTENCE AND A METHOD FOR MANUFACTURING THE SAME

This is a divisional of Application Ser. No. 09/830,010, filed Apr. 19, 2001, now U.S. Pat. No. 6,680,075

TECHNICAL FIELD

The present invention relates to natural invigorating, tea products and a method for preparing the same. More particularly, the present invention relates to invigorative teas made of certain parasitic plants, alder and/or schizandra and a method for preparing the same.

PRIOR ART

Human beings are mentally and physically affected by various external and internal factors. Those factors are, weather, biosocial environments and nutritional conditions. Occasionally, the effect is exerted as a stress on the human body. Stress is said to be a stimulus or succession of stimuli of such magnitude as to tend to disrupt the homeostasis of the organism. In these days of multifunctional information-oriented society, human beings undergo various stresses, caused by physical, chemical and biological or emotional stimuli. Recent reports have revealed that men who are under severe or extensive stress become poor in virility due to reduction in their sperm concentration and sperm motility.

Generally, sperm motility is taken as an indicator for sperm viability (Noran et al., 1998), while semen motility is evaluated in terms of sperm concentration, percentage of morphologically abnormal sperms, ratio of living to dead sperm, semen volume, pH, initial vitality of sperms, and mass movement of sperms (Berndtson and Pickett, 1980).

After making an examination of sperm conditions of 50 persons in their twenties (24 years old on the average) and 44 persons aged 37–53 (42 years old on the average), who lived near Tokyo, Japan, the Medical College of Tokyo University, Japan, made a research report which contained a surprising result that the men in their forties had about 84 million sperm cells per ml on the average while the men in their twenties had a sperm count of as low as 46 millions, which is only 55% of the 40–49 age group's average. Also, it is found in the research report that all of the men aged around forty were capable of procreation by the criteria reported by WHO in 1992 that the minimum sperm count for conception through ordinary sexual intercourse must amount to 20 million per ml, whereas only 86% of the men in their twenties satisfied this criteria. Similar sperm motilities were detected in the men in their twenties and forties: 27% and 28%, respectively. However, sperms produced by the men in their twenties were measured to have a normal morphological ratio of 52%, which was lower than that of the men in their forties, measured to be 64%.

Also, the research report disclosed that the average sperm count of the men in their twenties and thirties had sharply reduced in comparison to that of men of the same ages 20 years ago, which were reported to have an average sperm count of 75 to 100 million in a similar research, adding that Japanese men had also suffered from the worldwide sperm count reduction phenomenon and that endocrine disruptors, called environmental hormones, had been deduced to play an important role in the sperm count reduction.

Indeed, it has been known that the average sperm count from human males is 60% lower compared with 50 years ago. According to the report made by Dr. Scott at the Copenhagen University Hospital in 1990, in a study for 14,000 men, it was found that the average sperm count was reduced to 66 million/ml with an average semen volume of 2.7 ml, representing a sharp reduction from the values of 110 million/ml and 3.9 ml respectively in 1940. This sperm count reduction phenomenon was also confirmed by Dr. Auger, in France. He said that average sperm counts had dropped to sixty million in 1992 from eighty nine millions in 1973 with a reduction rate of 2.1% per year.

If the sperm counts of men continue to drop at this rate, mankind will face a sterility crisis, threatening its continued existence, within 60 years.

Having been regarded as a symbol of masculinity, being vigorous or having stamina is helpful in maintaining men's health, as well as in their having sexual intercourse for preservation of the species or for pleasure.

Amid the current deluge of processed foods seasoned with chemicals, especially precooked foods, people tend to avoid natural foods. However, it is well known that one of the methods to retain the spirit and energy received from the natural system is to maintain a regimen of eating natural foods.

Artificially synthesized chemicals for use in industry and agriculture have long been known to have an abnormal influence on the workings of the endocrine systems of human beings and animals. Indeed, animals which are problematic in development, behavior or genital morphology owing to endocrine disruption, are now frequently found. This matter of grave concern is highly apt to happen to human beings. The chemicals are generically called endocrine disruptors, more well known as environmental hormones.

On the other hand, with an increase in interest about sex, some people seek to enhance their sexual potency by means of drugs or the like. In response to this tendency, a number of drugs are now commercially available. For example, medications have been developed to treat erectile dysfunction (impotence) in men. Also, people can obtain cream formulations to enhance sensual pleasure. In addition, it is suggested that alcohol improves human sex life because of its ability to relieve the tension of the nervous system. However, such drugs have many problems. The medication for treating impotence may be fatal to those who suffer from hypertension. Cream formulations are inconvenient for use in addition to being expensive. Alcohol users may be in danger of falling into alcoholism.

DISCLOSURE OF THE INVENTION

In order to solve the above problems, the present invention has an object of providing invigorating tea products made of natural herbs.

It is another object of the present invention to provide food products which is invigorative and inexpensive.

In one aspect of the present invention, there are provided natural invigorating tea products, comprising parasitic plants and alder and/or *schizandrae* as primary materials, which may be powdered, chipped or extracted and mixed with each other with a certain mixing ratio.

In another aspect of the present invention, there is provided a method for preparing natural invigorating tea products, in which additional herbal materials comprising *torilis fructus* and *polygala* are used. The products of the present invention have been found to show satisfactory effects when taken at least twice a day.

BEST MODES FOR CARRYING OUT THE INVENTION

The present invention provides natural tea products made of an extract of a first material comprising or selected from a group of certain parasitic plants and a second material of *schizandra* and/or leaf, sprig, root or fruit of alder, in which root, leaf or stem of *polygala japonica* Houtt and/or fruit or root of *torilis japonica* (Houttvkn) Dc. may be added or mixed, and a method for preparing the same.

The present invention also provides natural tea products made of an extract of a material comprising or selected from a group of certain parasitic plants, and an extract of leaf, branch, root or fruit of alder, or an extract of *schizandra*, in which an extract from root, leaf or stem of *polygala* and/or an extract from fruit or root of *torilis*, and a method for preparing the same.

The parasitic plants for use in this invention include *Boschniakia rossica* (Cham. Et Schlecht) Fedtsch. et Fierov. (hereinafter referred to *Boschniakia rossica* Fedtsch.) being parasitized on alder, *Orobanche coerulescens* Steph. and *Lathraea japonica* Miq.

Each whole body of the above parasitic plants is known to be used for a material in herbal medicines for energizing and invigorating human bodies or for a drugstuff for the treatment of paralysis.

Various alder species may be used in the present invention. In particular, the species named *Alnus japonica* Steud. and Alni cortex et *ramulus* are useful in the present invention. Abundant in tannic materials in its leaves, sprig, roots, and fruits, alder is known to be effective for protecting gastric mucosa.

*Schizandrae* fructus is known with its scientific name of *Schizandra chinensis* Baillon.

*Schizandra* fruits are known to aid recovery of eyesight and to relieve the body of fatigue because they are rich in organic acids and saponin.

In addition, *polygala japonica herba*, scientifically named *Polygala japonica* Houtt., and *torilis fructus*, scientifically named *Torilis japonica* (Houtt.) Decandolle, are found to be effective in augmenting or aiding the invigorating effects of the above plants or herbs.

*Polygala japonica herba*, a perennial herb belonging to *Polygalaceae*, contains saponin in the root and is prescribed in herbal medicines to relieve asthma.

With essential oil and coumarine in its fruits, *torilis fructus* is known to be germicidal and insecticidal. Further, extracts from its fruit and root are generally used in herbal medicine to treat gynaecological disorders.

While already known for their individual herbal effects, the ingredients of the present invention complementarily exert their medicinal effects with each other. For instance, the invigorating and energizing effect of the parasitic plants is further enhanced or complemented by alder and *schizandrae fructus*. A synergistic effect for the parasitic herbs also can be obtained from *torilis fructus* and *polygala japonica herba*.

A better understanding of the present invention may be obtained in light of the following examples which are claimed to illustrate, but are not to be construed to limit the present invention.

EXAMPLE 1

Preparation of Extract from *Boschniakia rossica* Fedtsch

After being washed and dried, the whole body of *Boschniakia rossica* Fedtsch. was finely chopped. 5 g of the chopped herb was steeped in a mixture of 130 ml of 95% ethanol and 330 ml of water at 35° C. for 4 hours, followed by evaporating the ethanol to give 300 ml of an extract.

Preparation of Extract from Leaves of *Alnus japonica* Steud

The leaves were finely chopped after being washed and dried. Using 4 g of the chopped leaves, an extract was obtained at an amount of 300 ml in the same manner as above.

Preparation of Natural Tea 300 ml of the extract prepared from *Boschniakia rossica* Fedtsch was mixed with 150 ml of the extract prepared from leaves of *Alnus japonica* Steud to give a natural tea of the present invention.

EXAMPLE 2

Preparation of Extract from *Boschniakia rossica* Fedtsch 300 ml of an extract from *Boschniakia rossica* Fedtsch, was obtained in the same manner as in Example 1.

Preparation of Extract from Sprig of *Alnus japonica* Steud

Sprigs of the alder were washed with water, dried and finely chopped, after which 300 ml of an extract was obtained from 6 g of the chopped stems in the same manner as in Example 1.

Preparation of Natural Tea 100 ml of the extract prepared from *Boschniakia rossica* Fedtsch, was mixed with 300 ml of the extract prepared from sprigs of *Alnus japonica* Steud to give a natural tea of the present invention.

EXAMPLE 3

Preparation of Extract from *Boschniakia rossica* Fedtsch.

300 ml of an extract from *Boschniakia rossica* Fedtsch was obtained in the same manner as in Example 1.

Preparation of Extract from Root of *Alnus japonica* Steud

Roots of the alder were washed with water, dried and finely chopped, after which 300 ml of an extract was obtained from 6 g of the chopped stems in the same manner as in Example 1.

Preparation of Natural Tea 300 ml of the extract prepared from *Boschniakia rossica* Fedtsch was mixed with 100 ml of the extract prepared from sprigs of *Alnus japonica* Steud to give a natural tea of the present invention, of the present invention.

EXAMPLE 4

Preparation of Extract from *Orobance coerulescens* Steph

After being washed and dried, the whole body of *Orobance coerulescens* Steph. was finely chopped, 6 g of the chopped herb was steeped in a mixture of 280 ml of 95% ethanol and 360 ml of water at 50° C. for 2 hours, followed by evaporating the ethanol to give 330 ml of an extract.

Preparation of Extract from Leave of *Alnus japonica* Steud

The leaves were finely chopped after being washed and dried. Using 4 g of the chopped leaves, an extract was obtained at an amount of 330 ml in the same manner as above.

Preparation of Natural Tea 150 ml of the extract prepared from *Orobanche coerulescens* Steph. was mixed with 250 ml of the extract prepared from leaves of *Alnus japonica* Steud to give a natural tea of the present invention.

EXAMPLE 5

Preparation of Extract from *Orobanche coerulescens* Steph 330 ml of an extract from *Orobanche coerulescens* Steph was obtained in the same manner as in Example 4.

Preparation of Extract from Sprigs of *Alnus japonica* Steud

Sprigs of the alder were washed with water, dried and finely chopped, after which 330 ml of an extract was obtained from 6 g of the chopped stems in the same manner as in Example 4.

Preparation of Natural Tea 250 ml of the extract prepared from *Orobanche coerulescens* Steph. was mixed with 50 ml of the extract prepared from sprigs of *Alnus japonica* Steud to give a natural tea of the present invention.

EXAMPLE 6

Preparation of Extract from *Orobanche coerulescens* Steph 330 ml of an extract was prepared from *Orobanche coerulescens* Steph in the same manner as in Example 4.

Preparation of Extract from Root of *Alnus japonica* Steud

Roots of the alder were washed with water, dried and finely chopped, after which 300 ml of an extract was obtained from 5 g of the chopped stems in the same manner as in Example 4.

Preparation of Natural Tea 200 ml of the extract prepared from *Orobanche coerulescens* Steph. was mixed with 100 ml of the extract prepared from sprigs of *Alnus japonica* Steud to give a natural tea of the present invention.

EXAMPLE 7

Preparation of Extract from *Lathraea japonica* Miq

After being washed and dried, the whole body of *Lathraea japonica* Miq. was finely chopped, 7 g of the chopped herb was steeped in a mixture of 80 ml of 95% ethanol and 330 ml of water at 60° C. for 6 hours, followed by evaporating the ethanol to give 330 ml of an extract.

Preparation of Extract from Leaves of *Alnus japonica* Steud

The leaves were finely chopped after being washed and dried. Using 4 g of the chopped leaves, an extract was obtained at an amount of 330 ml in the same manner as above.

Preparation of Natural Tea 200 ml of the extract prepared from *Lathraea japonica* Miq. was mixed with 150 ml of the extract prepared from leaves of *Alnus japonica* Steud to give a natural tea of the present invention.

EXAMPLE 8

Preparation of Extract from *Lathraea japonica* Miq 300 ml of an extract from *Lathraea japonica* Miq. was obtained in the same manner as in Example 7.

Preparation of Extract from Sprig of *Alnus japonica* Steud

Sprigs of the alder were washed with water, dried and finely chopped, after which 300 ml of an extract was obtained from 6 g of the chopped stems in the same manner as in Example 7.

Preparation of Natural Tea 150 ml of the extract prepared from *Lathraea japonica* Miq. was mixed with 150 ml of the extract prepared from sprigs of *Alnus japonica* Steud to give a natural tea of the present invention.

EXAMPLE 9

Preparation of Extract from *Lathraea japonica* Miq 300 ml of an extract was prepared from *Lathraea japonica* Miq. in the same manner as in Example 7.

Preparation of Extract from Root of *Alnus japonica* Steud

Roots of the alder were washed with water, dried and finely chopped, after which an extract was obtained from 5 g of the chopped stems in the same manner as in Example 7.

Preparation of Natural Tea 100 ml of the extract prepared from *Lathraea japonica* Miq. was mixed with 200 ml of the extract prepared from sprigs of *Alnus japonica* Steud to give a natural tea of the present invention.

EXAMPLE 10

Preparation of Extract from *Boschniakia rossica* Fedtsch

After being washed and dried, the whole body of *Boschniakia rossica* Fedtsch. was finely chopped. 5 g of the chopped herb was steeped in 330 ml of water at 65° C. for 9 hours to give 300 ml of an extract.

Preparation of Extract from Leave of *Alnus japonica* Steud

The leaves were finely chopped after being cleaned and dried. Using 4 g of the chopped leaves, an extract was obtained at an amount of 300 ml in the same manner as above.

Preparation of Natural Tea 250 ml of the extract prepared from *Boschniakia rossica* Fedtsch was mixed with 250 ml of the extract prepared from leaves of *Alnus japonica* Steud to give a natural tea of the present invention.

EXAMPLE 11

Preparation of Extract from *Boschniakia rossica* Fedtsch 300 ml of an extract from *Boschniakia rossica* Fedtsch. was obtained in the same manner as in Example 10.

Preparation of Extract from Sprig of *Alnus japonica* Steud

Sprigs of the alder were washed with water, dried and finely chopped, after which 300 ml of an extract was obtained from 6 g of the chopped stems in the same manner as in Example 10.

Preparation of Natural Tea 150 ml of the extract prepared from *Boschniakia rossica* Fedtsch. was mixed with 200 ml of the extract prepared from sprigs of *Alnus japonica* Steud to give a natural tea of the present invention.

EXAMPLE 12

Preparation of Extract from *Boschniakia rossica* Fedtsch 300 ml of an extract from *Boschniakia rossica* Fedtsch. was obtained in the same manner as in Example 10.

Preparation of Extract from Root of *Alnus japonica* Steud

Roots of the alder were washed with water, dried and finely chopped, after which 300 ml of an extract was obtained from 5 g of the chopped stems in the same manner as in Example 10.

Preparation of Natural Tea 250 ml of the extract prepared from *Boschniakia rossica* Fedtsch. was mixed with 50 ml of the extract prepared from sprigs of *Alnus japonica* Steud to live a natural tea of the present invention.

EXAMPLE 13

Preparation of Extract from *Orobance coerulescens* Steph

After being washed and dried, the whole body of *Orobance coerulescens* Steph. was finely chopped. 6 g of the chopped herb was steeped in 360 ml of water at 75° C. for 8 hours to give 330 ml of an extract.

Preparation of Extract from Leaves of *Alnus japonica* Steud

The leaves were finely chopped after being washed and dried. Using 4 g of the chopped leaves, an extract was obtained at an amount of 330 ml in the same manner as above.

Preparation of Natural Tea 330 ml of the extract prepared from *Orobanche coerulescens* Steph. was mixed with 160 ml of the extract prepared from leaves of *Alnus japonica* Steud to give a natural tea of the present invention.

EXAMPLE 14

Preparation of Extract from *Orobanche coerulescens* Steph 330 ml of an extract from *Orobanche coerulescens* Steph. was obtained in the same manner as in Example 13.

Preparation of Extract from Sprig of *Alnus japonica* Steud

Sprigs of the alder were washed with water, dried and finely chopped, after which 330 ml of an extract was obtained from 6 g of the chopped stems in the same manner as in Example 13.

Preparation of Natural Tea 110 ml of the extract prepared from *Orobanche coerulescens* Steph. was mixed with 220 ml of the extract prepared from sprigs of *Alnus japonica* Steud to give a natural tea of the present invention.

EXAMPLE 15

Preparation of Extract from *Orobanche coerulescens* Steph 330 ml of an extract was prepared from *Orobanche coerulescens* Steph. in the same manner as in Example 13.

Preparation of Extract from Root of *Alnus japonica* Steud

Roots of the alder were washed with water, dried and finely chopped, after which an extract was obtained from 5 g of the chopped stems in the same manner as in Example 13.

Preparation of Natural Tea 200 ml of the extract prepared from *Orobanche coerulescens* Steph. was mixed with 110 ml of the extract prepared from sprigs of *Alnus japonica* Steud to give a natural tea of the present invention.

EXAMPLE 16

Preparation of Extract from *Lathraea japonica* Miq

After being washed and dried, the whole body of *Lathraea japonica* Miq. was finely chopped. 7 g of the chopped herb was steeped in 330 ml of water at 85° C. for 7 hours to give 300 ml of an extract.

Preparation of Extract from Leaves of *Alnus japonica* Steud

The leaves were finely chopped after being washed and dried. Using 4 g of the chopped leaves, an extract was obtained at an amount of 300 ml in the same manner as above.

Preparation of Natural Tea 50 ml of the extract prepared from *Lathraea japonica* Miq. was mixed with 250 ml of the extract prepared from leaves of *Alnus japonica* Steud to give a natural tea of the present invention.

EXAMPLE 17

Preparation of Extract from *Lathraea japonica* Miq 300 ml of an extract from *Lathraea japonica* Miq. was obtained in the same manner as in Example 16.

Preparation of Extract from Sprig of *Alnus japonica* Steud

Sprigs of the alder were washed with water, dried and finely chopped, after which 300 ml of an extract was obtained from 6 g of the chopped stems in the same manner as in Example 16.

Preparation of Natural Tea 250 ml of the extract prepared from *Lathraea japonica* Miq. was mixed with 50 ml of the extract prepared from sprigs of *Alnus japonica* Steud to give a natural tea of the present invention.

EXAMPLE 18

Preparation of Extract from *Lathraea japonica* Miq 300 ml of an extract was prepared from *Lathraea japonica* Miq. in the same manner as in Example 16.

Preparation of Extract from Root of *Alnus japonica* Steud

Roots of the alder were washed with water, dried and finely chopped, after which an extract was obtained from 5 g of the chopped stems in the same manner as in Example 16.

Preparation of Natural Tea 200 ml of the extract prepared from *Lathraea japonica* Miq. was mixed with 100 ml of the extract prepared from sprigs of *Alnus japonica* Steud to give a natural tea of the present invention.

EXAMPLE 19

Preparation of Extract from *Boschniakia rossica* Fedtsch 300 ml of an extract was prepared from *Boschniakia rossica* Fedtsch. in the same manner as in Example 1.

Preparation of Extract from Mixture of Alder Leave and *Schizandrae Fructus*

After being washed with water and dried, alder leaves and *schizandrae fructus* were crushed separately and mixed together with 2 g and 3 g, respectively. From the mixture, an extract was obtained in the same manner as in Example 1.

Preparation of Natural Tea 200 ml of the extract prepared from *Boschniakia rossica* Fedtsch. was mixed with 150 ml of the extract from a mixture of alder leaves and *schizandrae fructus* to give a natural tea of the present invention.

EXAMPLE 20

Preparation of Extract from *Orobanche coerulescens* Steph 330 ml of an extract was prepared from *Orobanche coerulescens* Steph. in the same manner as in Example 4.

Preparation of Extract from *schizandrae fructus*

*Schizandrae fructus* was washed with water, dried and crushed, after which an extract was obtained from 5 g of the crushed fruits in the same manner as in Example 4.

Preparation of Natural Tea 150 ml of the extract prepared from *Orobanche coerulescens* Steph. was mixed with 150 ml of the extract from *schizandrae fructus* to give a natural tea of the present invention.

EXAMPLE 21

Preparation of Extract from *Lathraea japonica* Miq 300 ml of an extract prepared from *Lathraea japonica* Miq. in the same manner as in Example 7.

Preparation of Extract from *schizandrae fructus*

*Schizandrae fructus* was washed with water, dried and crushed, after which an extract was obtained from 5 g of the crushed fruits in the same manner as in Example 7.

Preparation of Natural Tea 100 ml of the extract prepared from *Lathraea japonica* Miq. was mixed with 200 ml of the extract from *schizandrae fructus* to give a natural tea of the present invention.

EXAMPLE 22

Preparation of Extract from *Boschniakia rossica* Fedtsch 300 ml of an extract prepared from *Boschniakia rossica* Fedtsch. in the same manner as in Example 10.

Preparation of Extract from *schizandrae fructus*

*Schizandrae fructus* was washed with water, dried and crushed, after which an extract was obtained from 5 g of the crushed fruits in the same manner as in Example 10.

Preparation of Natural Tea 50 ml of the extract prepared from *Boschniakia rossica* Fedtsch. was mixed with 250 ml of the extract from *schizandrae fructus* to give a natural tea of the present invention.

EXAMPLE 23

Preparation of Extract from *Orobanche coerulescens* Steph 330 ml of an extract was prepared from *Orobanche coerulescens* Steph. in the same manner as in Example 13.

Preparation of Extract from Mixture of Alder Sprig and *schizandrae fructus*

After being washed with water and dried, alder sprigs and *schizandrae fructus* were crushed separately, followed by mixing 2.5 g of each of the crushed herbs together. From the mixture, an extract was obtained in the same manner as in Example 13.

Preparation of Natural Tea 150 ml of the extract prepared from *Orobanche coerulescens* Steph. was mixed with 200 ml of the extract from a mixture of alder leaves and *schizandrae fructus* to give a natural tea of the present invention.

EXAMPLE 24

Preparation of Extract from *Lathraea japonica* Miq 300 ml of an extract prepared from *Lathraea japonica* Miq. in the same manner as in Example 16.

Preparation of Extract from *schizandrae fructus*

*Schizandrae fructus* was washed with water, dried and crushed, after which an extract was obtained from 5 g of the crushed fruits in the same manner as in Example 16

Preparation of Natural Tea 250 ml of the extract prepared from *Lathraea japonica* Miq. was mixed with 50 ml of the extract from *schizandrae fructus* to give a natural tea of the present invention.

EXAMPLE 25

Preparation of Extract from *torilis fructus*

After being washed and dried, fruits of *torilis fructus* were crushed. The crushed fruits were steeped in a mixture of 130 ml of 95% ethanol and 330 ml of water at 35° C. for 4 hours, followed by evaporating the ethanol to give 300 ml of an extract.

Preparation of Natural Tea 100 ml of the extract from *torilis fructus* fruits was mixed with 50 ml of the extract from *Boschniakia rossica* Fedtsch. and 200 ml of the extract from alder leaves, both prepared in Example 1, to give a natural tea of the present invention.

EXAMPLE 26

200 ml of the extract from *Boschniakia rossica* Fedtsch. and 250 ml of the extract from alder sprigs, both prepared in Example 2, were mixed with 150 ml of the extract prepared from *torilis fructus* fruits in Example 25 to give a natural tea of the present invention.

EXAMPLE 27

100 ml of the extract from *Boschniakia rossica* Fedtsch., 100 ml of the extract from alder roots, both extracts prepared in Example 3, 50 ml of the extract prepared from *schizandrae fructus* in Example 20, and 200 ml of the extract prepared from *torilis fructus* fruits in Example 25 were mixed to give a natural tea of the present invention.

EXAMPLE 28

50 ml of the extract from *Orobanche coerulescens* Steph., 150 ml of the extract from alder leaves, both extracts prepared in Example 4, and 150 ml of the extract prepared from *torilis fructus* fruits in Example 25 were mixed to give a natural tea of the present invention.

EXAMPLE 29

150 ml of the extract from *Lathraea japonica* Miq. 100 ml of the extract from alder sprigs, both extracts prepared in Example 8, and 250 ml of the extract prepared from *torilis fructus* fruits in Example 25 were mixed to give a natural tea of the present invention.

EXAMPLE 30

100 ml of the extract from *Boschniakia rossica* Fedtsch., 100 ml of the extract from alder leaves, both extracts prepared in Example 10, and 150 ml of the extract prepared from *torilis fructus* fruits in Example 25 were mixed to give a natural tea of the present invention.

EXAMPLE 31

300 ml of the extract from *Orobanche coerulescens* Steph., 50 ml of the extract from alder roots, both extracts prepared in Example 15, and 50 ml of the extract prepared from *torilis fructus* fruits in Example 25 were mixed to give a natural tea of the present invention.

EXAMPLE 32

50 ml of the extract from *Lathraea japonica* Miq., 50 ml of the extract from alder sprigs, both extracts prepared in Example 17, and 200 ml of the extract prepared from *torilis fructus* fruits in Example 25 were mixed to give a natural tea of the present invention.

EXAMPLE 33

50 ml of the extract from *Boschniakia rossica* Fedtsch., 50 ml of the extract from a mixture of alder sprigs and *schizandrae fructus,* both extracts prepared in Example 19, and 200 ml of the extract prepared from *torilis fructus* fruits in Example 25 were mixed to give a natural tea of the present invention.

EXAMPLE 34

50 ml of the extract from *Lathraea japonica* Miq., 250 ml of the extract from *schizandrae fructus,* both extracts prepared in Example 21, and 100 ml of the extract prepared from *torilis fructus* fruits in Example 25 were mixed to give a natural tea of the present invention.

EXAMPLE 35

100 ml of the extract from *Orobanche coerulescens* Steph., 100 ml of the extract from a mixture of alder sprigs and *schizandrae fructus,* both extracts prepared in Example 23, 100 ml of an extract prepared from alder roots in Example 3, and 100 ml of the extract prepared from *torilis fructus* fruits in Example 25 were mixed to give a natural tea of the present invention.

EXAMPLE 36

50 ml of the extract from *Lathraea japonica* Miq., 50 ml of the extract from *schizandrae fructus,* both extracts prepared in Example 24, and 100 ml of the extract prepared from *torilis fructus* fruits in Example 25 were mixed to give a natural tea of the present invention.

EXAMPLE 37

Preparation of Extraction from *polygalae japonica herba* Roots

After being washed and dried, *polygalae japonica* herba roots were finely chopped. 5 g of the chopped herb was steeped in a mixture of 130 ml of 95% ethanol and 330 ml of water at 35° C. for 4 hours, followed by evaporating the ethanol to give 300 ml of an extract.

Preparation of Natural Tea 150 ml of the extract from *polygalae japonica herba* roots was mixed with 50 ml of the extract from *Boschniakia rossica* Fedtsch. and 200 ml of the extract from alder leaves, both prepared in Example 1, to give a natural tea of the present invention.

EXAMPLE 38

200 ml of the extract from *Boschniakia rossica* Fedtsch., 250 ml of the extract from alder sprigs, both extracts prepared in Example 2, and 100 ml of the extract prepared from *polygalae japonica herba* roots in Example 37 were mixed to give a natural tea of the present invention.

EXAMPLE 39

100 ml of the extract from *Boschniakia rossica* Fedtsch., 150 ml of the extract from alder roots, both extracts prepared in Example 3, and 100 ml of the extract prepared from *polygalae japonica herba* roots in Example 37 were mixed to give a natural tea of the present invention.

EXAMPLE 40

50 ml of the extract from *Orobanche coerulescens* Steph., 150 ml of the extract from alder leaves, both extracts prepared in Example 4, and 200 ml of the extract prepared from *polygalae japonica herba* roots in Example 37 were mixed to give a natural tea of the present invention.

EXAMPLE 41

200 ml of the extract from *Boschniakia rossica* Fedtsch., 250 ml of the extract from alder sprigs, both extracts prepared in Example 8, and 250 ml of the extract prepared from *polygalae japonica herba* roots in Example 37 were mixed to give a natural tea of the present invention.

EXAMPLE 42

100 ml of the extract from *Orobanche coerulescens* Steph., 100 ml of the extract from alder leaves, both extracts prepared in Example 10, and 100 ml of the extract prepared from *polygalae japonica herba* roots in Example 37 were mixed to give a natural tea of the present invention.

EXAMPLE 43

300 ml of the extract from *Orobanche coerulescens* Steph., 50 ml of the extract from alder roots, both extracts prepared in Example 15, and 100 ml of the extract prepared from *polygalae japonica herba* roots in Example 37 were mixed to give a natural tea of the present invention.

EXAMPLE 44

50 ml of the extract from *Lathraea japonica* Miq., 250 ml of the extract from alder sprigs, both extracts prepared in Example 17, and 250 ml of the extract prepared from *polygalae japonica herba* roots in Example 37 were mixed to give a natural tea of the present invention.

EXAMPLE 45

200 ml of the extract from *Boschniakia rossica* Fedtsch., 250 ml of the extract from a mixture of alder leaves and *schizandrae fructus,* both extracts prepared in Example 19, and 200 ml of the extract prepared from *polygalae japonica herba* roots in Example 37 were mixed to give a natural tea of the present invention.

EXAMPLE 46

150 ml of the extract from *Lathraea japonica* Miq., 250 ml of the extract from *schizandrae fructus,* both extracts prepared in Example 8, and 100 ml of the extract prepared from *polygalae japonica herba* roots in Example 37 were mixed to give a natural tea of the present invention.

EXAMPLE 47

100 ml of the extract from *Orobanche coerulescens* Steph., 100 ml of the extract from a mixture of alder sprigs and *schizandrae fructus,* both extracts prepared in Example 23, and 100 ml of the extract prepared from *polygalae japonica herba* roots in Example 37 were mixed to give a natural tea of the present invention.

EXAMPLE 48

250 ml of the extract from *Lathraea japonica* Miq., 50 ml of the extract from alder sprigs, both extracts prepared in Example 24, and 100 ml of the extract prepared from *polygalae japonica herba* roots in Example 37 were mixed to give a natural tea of the present invention.

Although 95% ethanol was used as an extractant, lower concentrations can also be used. The only difference is the period of time required to extract useful ingredients from herbs.

In the following examples, natural tea products were prepared by carrying out an extraction process on the parasite herbs, which are indispensable to achieve the present invention, along with the other herbal materials.

EXAMPLE 49

*Boschniakia rossica* Fedtsch. and alder leaves were separately washed with water, dried and cut into small pieces, after which 4 g of the chopped *Boschniakia rossica* Fedtsch. and 5 g of the chopped alder leaves were steeped in a mixture of 100 ml of 95% ethanol and 650 ml of water at 60° C. for 6 hours to give 600 ml of a natural tea of the present invention.

EXAMPLE 50

*Orobanche coerulescens* Steph. and alder sprigs were separately washed with water, dried and cut into small pieces, after which 6 g of the chopped *Orobanche coerulescens* Steph. and 6 g of the chopped alder sprigs were steeped in a mixture of 200 ml of 95% ethanol and 650 ml of water at 50° C. for 6 hours, followed by evaporating the ethanol to give 600 ml of a natural tea of the present invention.

EXAMPLE 51

*Lathraea japonica* Miq. and alder roots were separately washed with water, dried and cut into small pieces, after which 7 g of the chopped *Lathraea japonica* Miq. and 5 g of the chopped alder roots were steeped in a mixture of 300 ml of 95% ethanol and 700 ml of water at 45° C. for 5 hours, followed by evaporating the ethanol to give 630 ml of a natural tea of the present invention.

EXAMPLE 52

After being washed with water and dried, *Boschniakia rossica* Fedtsch. and *schizandrae fructus* were cut into small pieces and crushed, respectively. 7 g of the chopped *Boschniakia rossica* Fedtsch. and 5 g of the crushed *schizandrae fructus* were steeped in a mixture of 100 ml of 95% ethanol and 700 ml of water at 65° C. for 8 hours to give 650 ml of a natural tea of the present invention.

EXAMPLE 53

After being washed with water and dried, *Orobanche coerulescens* Steph. and *schizandrae fructus* were cut into small pieces and crushed, respectively. 5 g of the chopped *Orobanche coerulescens* Steph. and 3 g of the crushed *schizandrae fructus* were steeped in 700 ml of water at 70° C. for 8 hours to give 650 ml of a natural tea of the present invention.

EXAMPLE 54

After being washed with water and dried, *Lathraea japonica* Miq. and *schizandrae fructus* were cut into small pieces and crushed, respectively. 8 g of the chopped *Lathraea japonica* Miq. and 2 g of the crushed *schizandrae fructus* were steeped in 700 ml of water at 80° C. for 7 hours to give 650 ml of a natural tea of the present invention.

EXAMPLE 55

*Boschniakia rossica* Fedtsch. and alder leaves were separately washed with water, dried and cut into small pieces while cleaned, dried *torilis fructus* was crushed. 1 g of the chopped *Boschniakia rossica* Fedtsch., 6 g of the chopped alder leaves roots and 2 g of the crushed *torilis fructus* were steeped in 500 ml of water at 75° C. for 8 hours to give 450 ml of a natural tea of the present invention.

EXAMPLE 56

While cleaned, dried *Orobanche coerulescens* Steph. was cut into small pieces, *schizandrae fructus* and *torilis fructus* were separately washed with water, dried and crushed. 2 g of the chopped *Orobanche coerulescens* Steph., 5 g of the crushed *schizandrae fructus* and 3 g of the crushed *torilis fructus* were steeped in 800 ml of water at 50° C. for 10 hours to give 750 ml of a natural tea of the present invention.

EXAMPLE 57

*Lathraea japonica* Miq. and *polygalae japonica herba* roots were separately washed with water, dried and cut into small pieces while cleaned, dried *schizandrae fructus* was crushed. 1 g of the chopped *Lathraea japonica* Miq., 1 g of the chopped *polygalae japonica herba* roots and 3 g of the crushed *schizandrae fructus* were steeped in 360 ml of water at 30° C. for 12 hours to give 360 ml of a natural tea of the present invention.

EXAMPLE 58

*Boschniakia rossica* Fedtsch. and *polygalae japonica herba* roots were separately washed with water, dried and cut into small pieces while cleaned, dried *schizandrae fructus* and *torilis fructus* were crushed. 1 g of the chopped *Boschniakia rossica* Fedtsch., 2 g of the chopped *polygalae japonica herba* roots, 5 g of the crushed *schizandrae fructus* and 3 g of *torilis fructus* were steeped in 900 ml of water at 90° C. for 6 hours to give 850 ml of a natural tea of the present invention.

In the above tea examples of preparing the natural tea products according to the present invention, it is noted that the same extractant, water or ethanol, was used for the different materials in each example as in the example 1 through 48. However, it is of course possible to use different extractants for the different materials or herbs adopted in the same example.

After hosts of experiments with various compositions of the parasitic plants and alder and/or *schizandrae fructus*, extracts comprising 20–80% by weight of the parasitic plants and correspondingly 80–20% by weight of alder and/or *schizandrae fructus* were found to be preferably effective in invigorating the body.

Also, a preferred invigorating effect could be obtained when *polygalae japonica herba* roots and/or *torilis fructus* was present at an amount of 10–70% by weight based on the total weight of the materials used.

As described above, the herbal materials can be steeped or extracted separately or in a mixture of them with a preference to an extraction ratio of 40–120 cc/g. As for the extractants, they must be aqueous and edible like water and ethanol. The extraction period of time depends on the concentration of ethanol in the extractant. It should be understood that the extraction period of time can not be a reason for limiting the scope of the present invention.

Of the parasitic herbs, the herbal material indispensable for the present invention, *Lathraea japonica* Miq. was found to be more effective in invigorating the body than the other two species, *Orobanche coerulescens* Steph. and *Boschniakia rossica* Fedtsch., the former being more effective than the latter.

Compared with a natural tea comprising an extract from either *polygalae japonica herba* roots or *torilis fructus*, a natural tea comprising extracts from both *polygalae japonica herba* roots and *torilis fructus* showed a further improved invigorating effect.

Differently from the above examples, the same materials as used in the above-described examples may be steamed and dried so as for the resulting mixture to be soaked in boiling water to give a natural tea according the present invention. Preferably, the mixture is freeze-dried. Alternatively, the mixture of the tea materials either in the natural state or in the steamed state may be powdered to give a natural tea according to the present invention as claimed in the accompanying claims.

As for the alder, all its parts, including fruits, sprigs, leaves and roots, were found to be effective although the fruit was not included in the above description and the alder extracts as described in the claims mean all parts of alder as above.

In addition to roots of *polygalae japonica herba*, its leaves and stems are useful in the present invention. Even in the case of *torilis fructus*, its roots as well as fruits were found to be effective in invigorating the body.

In order to improve the taste or flavor of the natural tea according to the present invention, additives such as sweeteners and flavorings may be added to it.

CONTROL EXAMPLE

*Boschniakia rossica* Fedtsch. was cleaned and chopped to pieces, after which 4 g of the chopped *Boschniakia rossica* Fedtsch. was steeped in a mixture of 250 ml of 95% ethanol and 160 ml of water at 60° C. for 6 hours to give 150 g of an extract.

Experimental Test

An experimental test was carried out to confirm the invigorating effect of the natural tea products of the present invention. Each of 87 men in their forties to seventies was allowed to drink 140 ml of a natural tea of this invention twice a day, after breakfast and just before sleeping for 30 days and then effects of the teas on the sex life the subjects were measured. For comparison, the tea prepared in Control Example was used as a control. The results are given in Table 1, below.

TABLE 1

| Natural Tea | Effectivness | Men's Age | | | |
|---|---|---|---|---|---|
| | | 40–49 | 50–59 | 60–69 | 70–79 |
| Control | Effective | 0 | 0 | | |
| | Ineffective | 6 | 6 | | |

TABLE 1-continued

| Natural Tea | Effectivness | \multicolumn{4}{c}{Men's Age} | | | |
|---|---|---|---|---|---|
| | | 40–49 | 50–59 | 60–69 | 70–79 |
| Example 1 | Effective | 6 | | | |
| | Ineffective | 1 | | | |
| Example 10 | Effective | 6 | | | |
| | Ineffective | 2 | | | |
| Example 29 | Effective | 7 | | | |
| | Ineffective | 1 | | | |
| Example 37 | Effective | 6 | 6 | | |
| | Ineffective | 1 | 1 | | |
| Example 57 | Effective | 5 | 5 | 5 | |
| | Ineffective | 0 | 1 | 1 | |
| Example 58 | Effective | 5 | 5 | 4 | 4 |
| | Ineffective | 0 | 1 | 1 | 1 |
| Total | Effective | 35 | 16 | 9 | 4 |
| | Ineffective | 5 | 3 | 2 | 1 |

As apparent from Table 1, the natural tea products prepared according to the present invention are effective in invigorating the body although the effect is dependent on subjects' physical and mental conditions, such as health, stamina and the like. The data of Table 1 also demonstrate that greater invigorating effects can be obtained from the natural teas supplemented with *torilis fructus* and/or *polygalae japonica* herba in, comparison to the natural teas comprising the parasite herb, and alder and/or *schizandrae fructus* only.

INDUSTRIAL APPLICABILITY

As described above, the present invention provides natural invigorating tea products in the form of powder, liquid, or granules, made of parasitic herb and alder and/or *schizandrae fructus,* optionally supplemented with *torilis fructus* and/or *polygalae japonica herba.* Drinking of the tea twice a day, morning and evening, improves human males' sexual potency. Another advantage of the present invention is that the tea can be prepared at low cost.

What is claimed is:

1. A method for preparing a natural invigorating tea, in whidi at least three herbal materials selected from the group consisting of a parasitic herb, Alder, *Schizandrae fructus, Polygalae japonica* herbs and *Torilis fructus* are first chopped and mixed together and then steamed, powdered or subjected to extraction treatment.

2. A method as claimed in claim 1, wherein the at least three herbal materials selected from the group consisting of a parasitic herb, Alder, *Schizandrae fructus, Polygalae japonica herba* and *Torilis fructus* are respectively used in an amount of 10–70% by weight.

3. A method as claimed in claim 1, wherein all or part of the herbal materials are used in a natural state.

4. A method as claimed in claim 1, wherein some or all of the herbal materials are subjected to a drying treatment.

5. A method as claimed in claim 4, wherein the drying treatment results in the herbal materials having moisture contents of 10–20%.

* * * * *